(12) United States Patent
Tortoli

(10) Patent No.: US 7,591,787 B2
(45) Date of Patent: Sep. 22, 2009

(54) METHOD FOR REMOVING DOPPLER ANGLE AMBIGUITY

(76) Inventor: Piero Tortoli, Via Santa Marta 3, Firenze (IT) 50139

( * ) Notice: Subject to any disclaimer, the term of this patent is extended or adjusted under 35 U.S.C. 154(b) by 405 days.

(21) Appl. No.: 11/227,662

(22) Filed: Sep. 15, 2005

(65) Prior Publication Data

US 2007/0073153 A1 Mar. 29, 2007

(51) Int. Cl.
- *A61B 1/00* (2006.01)
- *A61B 5/02* (2006.01)
- *A61B 6/08* (2006.01)
- *A61B 8/06* (2006.01)

(52) U.S. Cl. .......... 600/454; 600/504; 600/505; 600/506; 600/507; 600/437; 600/453; 600/455; 600/456; 600/457; 73/861.25; 367/90

(58) Field of Classification Search ........ 600/454, 600/438, 441, 453, 458, 459
See application file for complete search history.

(56) References Cited

U.S. PATENT DOCUMENTS

| 4,103,679 A | * | 8/1978 | Aronson ............ 600/456 |
| 4,127,842 A | | 11/1978 | Hassler |
| 5,249,577 A | | 10/1993 | Shinomura et al. |
| 5,375,600 A | | 12/1994 | Melton, Jr. et al. |
| 5,386,830 A | | 2/1995 | Powers et al. |
| 5,409,010 A | * | 4/1995 | Beach et al. ......... 600/455 |
| 5,443,071 A | | 8/1995 | Banjanin et al. |
| 5,485,843 A | | 1/1996 | Greenstein et al. |
| 5,562,098 A | | 10/1996 | Lerner |
| 5,606,972 A | | 3/1997 | Routh |
| 5,701,898 A | | 12/1997 | Adam et al. |
| 5,769,079 A | | 6/1998 | Hossack |

(Continued)

FOREIGN PATENT DOCUMENTS

EP 0150672 8/1985

(Continued)

OTHER PUBLICATIONS

Tiziano Morganti, et al., "Clinical Validation of Common Carotid Artery Wall Distension Assessment Based on Multigate Doppler Processing," Ultrasound in Med & Biol., vol. 31, No. 7, pp. 937-945, 2005.

(Continued)

*Primary Examiner*—Long V Le
*Assistant Examiner*—Vani Gupta
(74) *Attorney, Agent, or Firm*—Amster, Rothstein & Ebenstein LLP

(57) ABSTRACT

A method of measuring blood flow including several steps. In an initial step a first ultrasound beam is oriented in a direction substantially perpendicular to the direction of the blood flow to be measured. Next, the Doppler spectrum obtained from the backscattered echoes of said first ultrasound beam is measured. Subsequently, the ultrasound beam is reoriented so that the Doppler spectrum of the backscattered echoes of the ultrasound beam is substantially symmetrical around the zero frequency. The Doppler frequency of the backscattered echoes of a second ultrasound beam oriented at a fixed angle to the first ultrasound beam is then measured. Finally, the rate of blood flow is calculated based on the angle between the ultrasound beams and the measured Doppler frequency of the backscattered echoes of the second ultrasound beam.

14 Claims, 6 Drawing Sheets

U.S. PATENT DOCUMENTS

| | | | |
|---|---|---|---|
| 5,800,358 | A | 9/1998 | Webb et al. |
| 5,928,153 | A * | 7/1999 | Chiang et al. ............... 600/454 |
| 6,142,944 | A | 11/2000 | Li et al. |
| 6,186,951 | B1 | 2/2001 | Lizzi et al. |
| 6,261,233 | B1 * | 7/2001 | Kantorovich ............... 600/454 |
| 6,293,913 | B1 | 9/2001 | Tsujino et al. |
| 6,318,179 | B1 * | 11/2001 | Hamilton et al. .............. 73/606 |
| 6,503,205 | B2 | 1/2003 | Manor et al. |
| 2002/0042574 | A1 | 4/2002 | Manor et al. |
| 2003/0144591 | A1 * | 7/2003 | Smith et al. ................. 600/437 |

FOREIGN PATENT DOCUMENTS

| | | |
|---|---|---|
| WO | PCT/IB06/03709ISR | 12/2007 |
| WO | PCT/IB06/03709WO | 12/2007 |

OTHER PUBLICATIONS

Giacomo Bambi, et al., "Real-Time Simultaneous Assessment of Wall Distension and Wall Shear Rate in Carotid Arteries," Universita di Firenze, Electronics & Telecommunications, Dept.

Daqing Piao, et al., "Doppler Angle and Flow Velocity Mapping by Combined Doppler Shift and Doppler Bandwidth Measurements in Optical Doppler Tomography," Optics Letter, vol. 28, No. 13, Jul. 1, 2003.

B. Dumire, et al., "Cross-Beam Vector DopplerUltrasound for Angle-Independent Velocity Measurements," Ultrasound in Med. & Biol., vol. 26, No. 8, pp. 1213-1235, 2000.

Piero Tortoli, et al., "Toward a Better Quantitative Measurement of Aortic Flow," Ultrasound in Med. & Biol., vol. 28, No. 2, Ipp. 249-257, 2002.

Daqing Piao and Quing Zhu, Quantifying Doppler Angle and Mapping Flow Velocity by a Combination of Doppler-Shift and Doppler-Bandwidth Measurements in Optical Doppler Tomography, Applied Optics, vol. 42, No. 25, Sep. 1, 2003.

King-Wah W. Yeung, "Angle —Insensitive Flow Measurement Using Doppler Bandwidth," HP Lab s Technical Reports, Mar. 17, 1997.

* cited by examiner

METHOD FOR REMOVING DOPPLER ANGLE AMBIGUITY

FIELD OF THE INVENTION

The present invention relates to the technical field of fluid flow rate measurement through the use of ultrasound, particularly in relation to blood flow.

DESCRIPTION OF RELATED ART

The use of ultrasound to measure blood flow is well known. According to the Doppler effect, a flow with velocity v impinged by a planar ultrasound (US) wave with centre frequency $f_0$, generates echoes characterized by a frequency shift:

$$f_1 = \frac{2f_0}{c}|v|\cos\theta \qquad \text{eqn. 1}$$

where c is the velocity of US and $\theta$ is the beam-to flow angle. By measuring the frequency $f_1$, the axial component, $|v|\times\cos\theta$, of the velocity magnitude, $|v|$, is estimated. However, as traditional Doppler methods only measure the axial component of the velocity vector, it is not possible to estimate the individual contribution of $|v|$ or $\theta$. The lack of information on the beam-to-flow angle creates an ambiguity which can lead to large errors in velocity magnitude estimates.

Several methods have been proposed to obtain angle independent blood velocity estimates. The standard approach is based on the combination of Doppler measurements taken along multiple US beams intersecting in the region of interest. The basic idea consists in measuring the Doppler frequencies received from the same sample volume (SV) insonified by two (or more) transducers whose beam axes are oriented along directions describing a known angle $\delta$. Through a trigonometric combination of the Doppler equations related to the frequencies obtained by the two transducers, both the velocity magnitude and the flow direction can be estimated.

SUMMARY OF THE INVENTION

The present invention proposes a new method for estimating the Doppler angle and the velocity magnitude, by using a configuration in which two ultrasound beams with known relative orientation are directed toward the same vessel. One of the beams is committed to perform a Doppler measurement, while a second (reference) beam has the specific task of detecting the beam-to-flow angle. A substantially perpendicular beam-to-flow angle can be obtained by reorienting the reference beam to obtain optimal spectral symmetry. Once the flow direction is known thanks to the reference beam, the velocity magnitude can be directly measured by the other ultrasound beam.

The two transducers of the invention perform completely different tasks: one transducer is used only to determine the flow direction, while the other has to perform a classic Doppler frequency measurement. This is possible by exploiting specific features of the Doppler spectrum, which are typical of the transverse beam-to-flow orientation.

One embodiment of the present invention is a system and method for measuring the rate of blood flow. In this embodiment a reference transducer is aligned to be substantially perpendicular to the blood flow to be measured. The symmetry of the Doppler spectra of the echoes backscattered to the reference transducer is measured and the transducer is reoriented so that the measured Doppler spectra is substantially symmetrical. A second ultrasonic transducer, oriented at a fixed angle to the reference transducer is then used to measure the Doppler frequency and the rate of blood flow is calculated based on these measurements and the known angle of the second transducer with respect to the direction of the blood flow.

The present invention can also be implemented using a linear array probe. In the linear array probe a first subaperture operates as the reference ultrasonic transducer and a second subaperture operates as the second ultrasonic transducer.

In at least one embodiment, the system further comprises an actuator for automatically reorienting the first ultrasonic transducer to an orientation substantially perpendicular to the rate of blood flow to be measured.

In an exemplary embodiment, the second subaperture is selectable from two or more subapertures.

A system for measuring the rate of blood flow according to an exemplary embodiment of the present invention comprises: a first ultrasonic transducer, a second ultrasonic transducer oriented at a fixed angle to the first ultrasonic transducer, a computer configured to determine when a Doppler frequency spectrum obtained from backscattered echoes of the first ultrasonic transducer is substantially symmetrical around a zero frequency, thereby indicating that a beam to flow angle of the first ultrasonic transducer is at approximately 90 degrees; a beam to flow angle of the second ultrasonic transducer based on the indicated beam to flow angle of the first ultrasonic transducer and the fixed angle; and means for calculating the rate of blood flow based upon the beam to flow angle of the second ultrasonic transducer and Doppler frequency of backscattered echoes of the second ultrasonic transducer.

In an exemplary embodiment, the computer generates a viewable graphical representation of the symmetry of the Doppler spectrum around the zero frequency.

In an exemplary embodiment, the computer generates a viewable numerical representation of the symmetry of the Doppler spectrum around the zero frequency.

In an exemplary embodiment, the first ultrasonic transducer comprises a first subaperture of a linear array probe, and the second ultrasonic transducer comprises a second subaperture of the linear array probe.

DETAILED DESCRIPTION

The present invention is a novel dual beam technique and system for performing that technique, which utilizes the specific features of Doppler spectra obtained at transverse beam-to-flow orientations. Unlike other approaches inspired by Newhouse's transverse Doppler theory, Doppler bandwidth does not have to be measured. By taking only the spectral symmetry into consideration for Doppler angle estimation, such angle could be estimated with errors lower than 1° through either subjective (operator dependent) and objective (SI-based) methods.

Classic cross-beam methods assume that the Doppler frequencies obtained from the two beams are due to the same velocity distribution, which is true only if the two transducers interrogate exactly the same SV. This goal, in general, is difficult to achieve, especially for non-spherical SVs and large interbeam angles. On the other hand, the performance is known to deteriorate as the angle between the beams is reduced.

The new method can be applied in any Doppler measurement in which a transverse insonification is compatible with the depth and the orientation of the vessel. The common carotid artery, being almost parallel to the skin, represents an ideal field of application for this technique. Both the reference beam and the measurement beam can be easily set along suitable directions through standard (steerable) linear array probes. The descending aorta, being almost parallel and quite close to the esophagus, is also suitable for application of the method when trans-esophageal probes are used.

Figure 1:
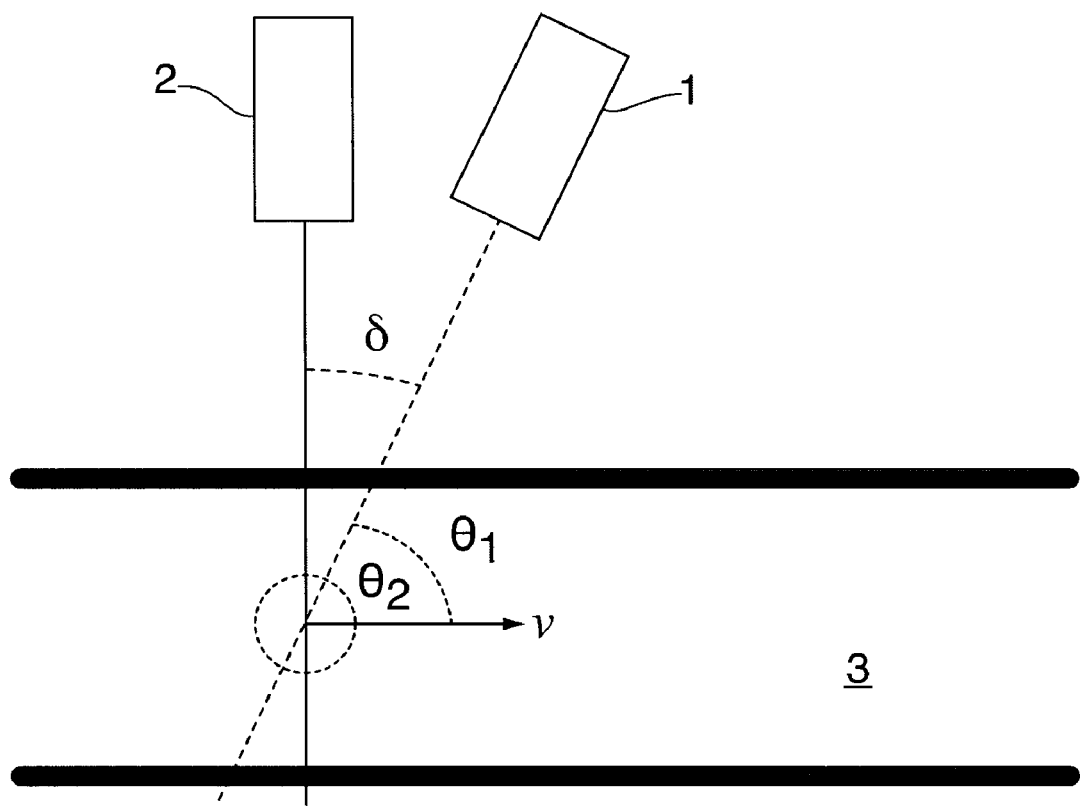
FIG. 1 illustrates the geometry of the dual-beam system.

As shown in FIG. 1, the system of the present invention has two ultrasonic transducers, a measuring transducer 1 and reference transducer 2, respectively, interrogating the same region of blood vessel 3 with beam-to-flow angles $\theta_1$ and $\theta_2$, respectively. The interbeam angle, $\delta$, is fixed at a predetermined angle.

The task of estimating the Doppler angle is performed through the reference transducer 2. The task of estimating the velocity magnitude is performed through the measuring transducer 1.

The reference beam-to-flow direction is uniquely determined by the characteristics of the Doppler spectrum obtained from the backscattered echoes of reference transducer 2. It is possible to evaluate such angle by analyzing how the Doppler spectral components are actually distributed.

Figure 2:
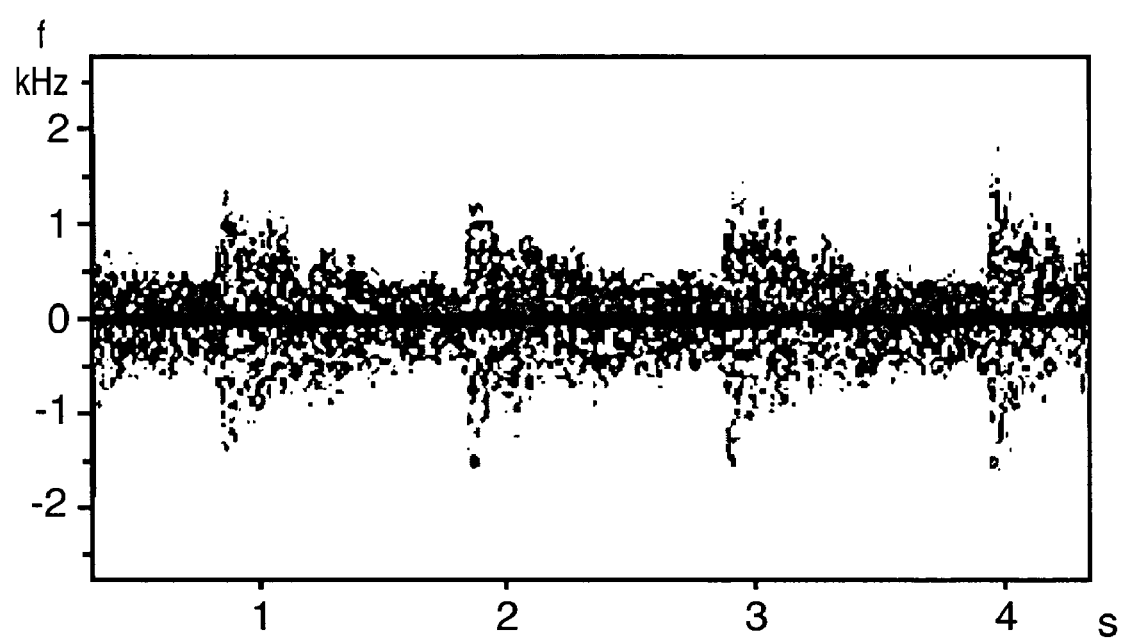
FIG. 2 illustrates a spectrogram obtained from a transversely insonated carotid artery.

The reference direction can be chosen substantially at 90° with respect to the flow being the Doppler spectrum of the backscattered echo in that direction substantially symmetrical around the zero frequency. FIG. 2 shows an example of such a substantially symmetrical Doppler spectrum. This property of the Doppler spectrum, is derived from the transducer focusing features, which involve a set of effective beam-to flow angles equally distributed around a nominal 90° angle.

Since the mean Doppler frequency of the received signal is related to the cosine of the nominal Doppler angle, a small deviation from the desired transverse orientation causes a visible loss of symmetry.

The extent at which the spectrum is actually symmetrical can be evaluated in different ways. For example, it can be based on the direct observation of the real time spectrogram.

To avoid any operator-dependence, the actual distribution of Doppler power between positive and negative sub-bands can be taken into consideration through the evaluation of a Symmetry index (SI) defined, e.g., as:

$$SI = \frac{\text{Doppler power distributed over positive frequencies}}{\text{Doppler power distributed over negative frequencies}} \times 100$$

in which the numerator and denominator are automatically exchanged when the ratio is >1. When $\theta_2=90°$, the SI should be ideally equal to 100%. However, since even a small deviation from 90° causes an appreciable loss of symmetry, a range of values lower than 100% can be considered acceptable. Preferably, $\theta_2$ should deviate from 90° by less than 2°. More preferably, $\theta_2$ should deviate from 90° by less than 1°.

In a preferred embodiment, reference transducer 1 may be automatically reoriented by an actuator to achieve a reference direction of substantially 90°. By monitoring the changes to the SI value for reference transducer 1, a computer system can send the appropriate signals to the actuator to adjust the orientation of reference transducer 1.

Finally, once the flow direction has been accurately determined, the beam-to-flow angle $\theta_1$ can be automatically determined by subtracting the known interbeam angle, $\delta$, from 90°.

Once the angle of insonation for the measurement beam, $\theta_1$, has been estimated, the mean velocity within the investigated SV can be directly evaluated through eqn. 1, in which $f_1$ represents the mean frequency of the selected Doppler signal. As a possible alternative, since the full Doppler spectrum is available, the local peak velocity can be estimated from:

$$V_{max} = \frac{f_{max}}{\frac{2f_0}{c}(\cos\theta_1 + k \times \sin\theta_1)} \qquad \text{eqn. 2}$$

in which $f_{max}$ is the spectrum peak frequency and k is a factor of proportionality depending on the transducer geometry. The second term in the denominator allows correcting for intrinsic spectral broadening effects.

The method of the present invention also provides advantages when used in conjunction with linear array probes. The optimal reference beam direction can be automatically set by tracking the steering angle which maximizes the spectral symmetry. This could be achieved by monitoring a symmetry index. Once the reference beam direction and the related SV depth have been fixed, the system can easily calculate the best options (in terms of position and steering angle) for the measuring beam, and automatically select the subaperture more suitable to generate such beam. These automatic procedures can be adapted to existing ultrasonic machines in order to obtain the benefits of the invention.

Figure 3:
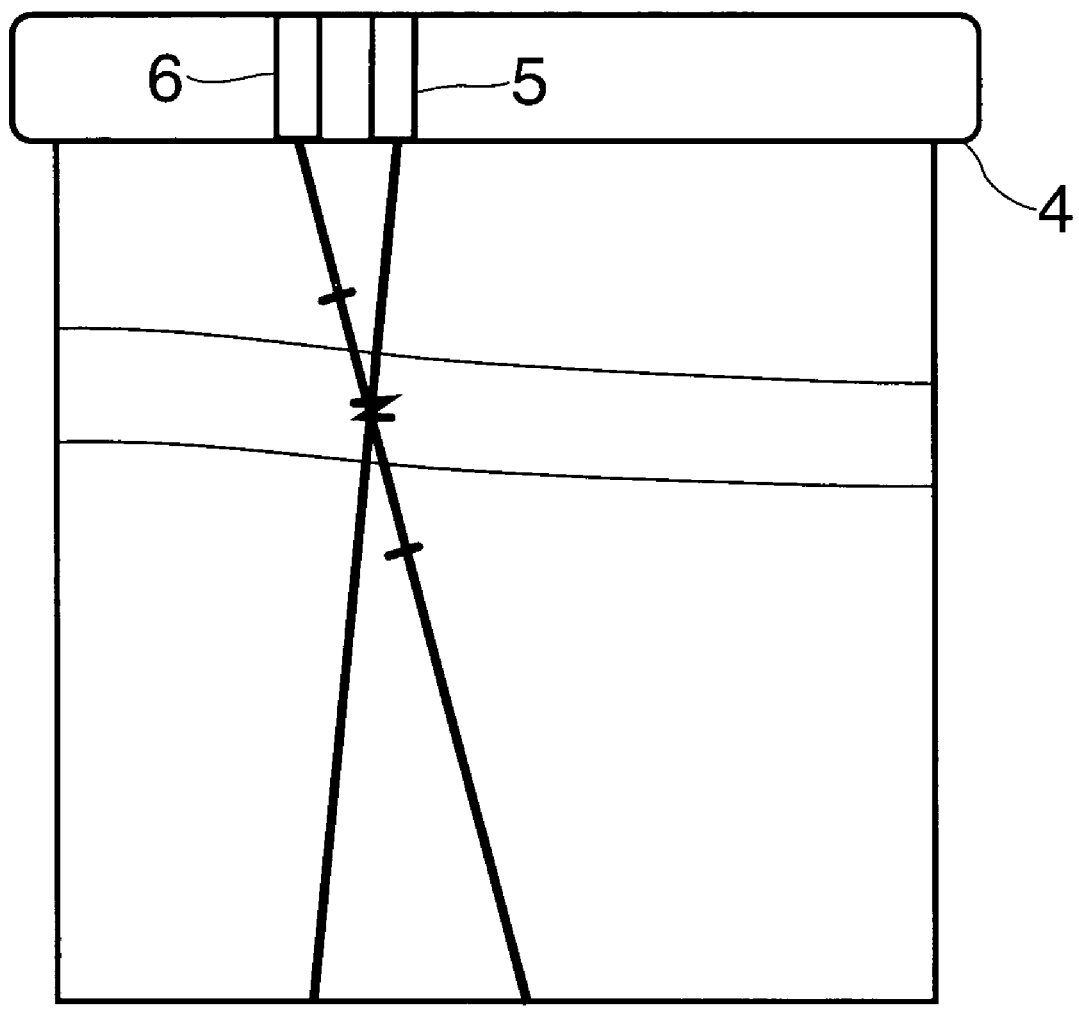
FIG. 3 illustrates a linear array probe operating over a blood vessel.

FIG. 3 shows a preferred embodiment of the invention in a system having a linear array probe 4. In this system, subaperture 5 is used to generate the reference beam and subaperture 6 is used to generate the measuring beam.

The teaching of the present invention is suitable for application in all systems employing spectral analysis for Doppler velocity measurement, including, in particular, multigate spectral Doppler systems. Although the invention has been described with reference to particular embodiments, there is no intention to restrict the scope of the invention, and indeed many other modifications and variations will be ascertainable to those of skill in the art.

EXAMPLE

The software of a commercial ultrasound machine (Megas by Esaote SpA, Florence, Italy) was customized to make possible the simultaneous selection of two independent M-lines in a standard B-mode display of the ROI as shown in FIG. 3.

The TX-RX process involves two independent subapertures of the linear array transducer. When switched to "Dual" PW-mode, the system fires the elements of the linear array probe in such a way that US bursts are alternatively transmitted from each sub-aperture. Echo signals backscattered from the SV intercepted by both such lines are processed so that the corresponding spectrograms are calculated and displayed on a PC screen in real-time.

The method of the present invention was tested in vitro by using a phantom in which it was possible to control the velocity for both steady and pulsatile flow conditions. Distilled water was forced to flow in a 10 mm internal diameter Rilsan tube. Orgasol particles were used for scattering purposes.

Figure 4:
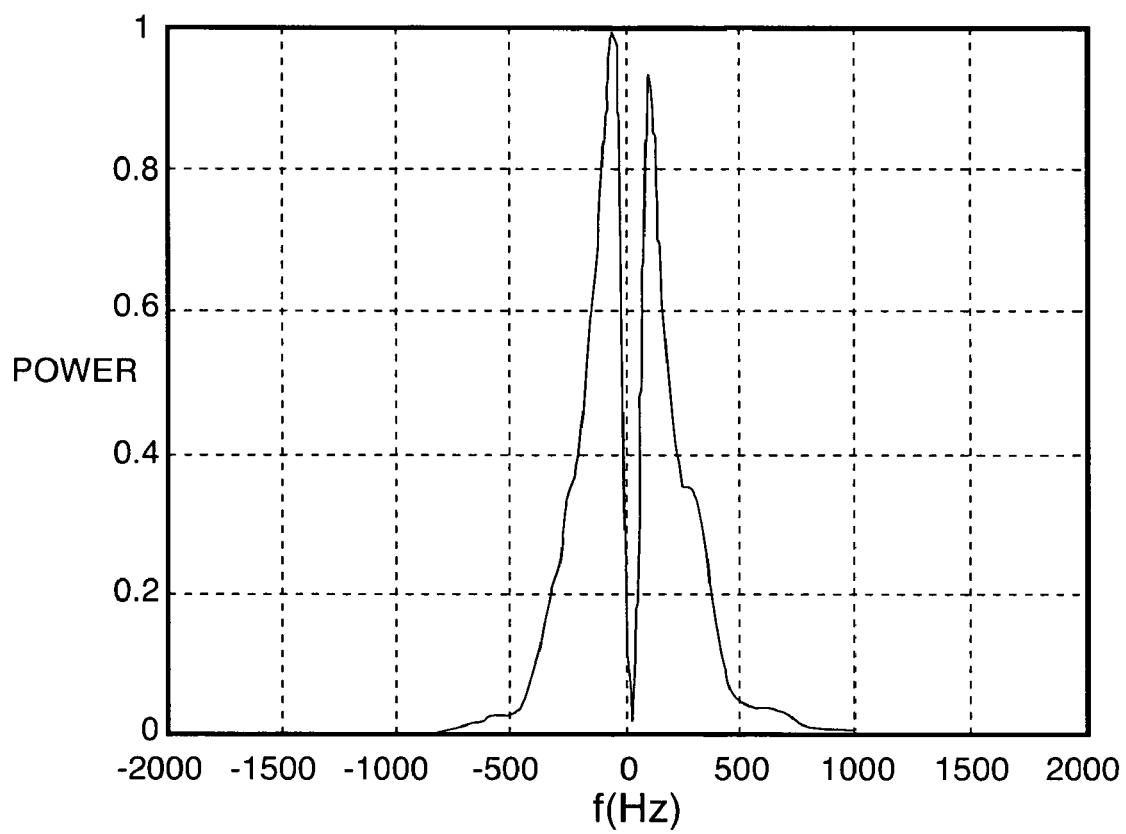
FIG. 4 illustrates ensemble averaged Doppler spectra obtained at a beam-vessel angle of 90°.
Figure 5:
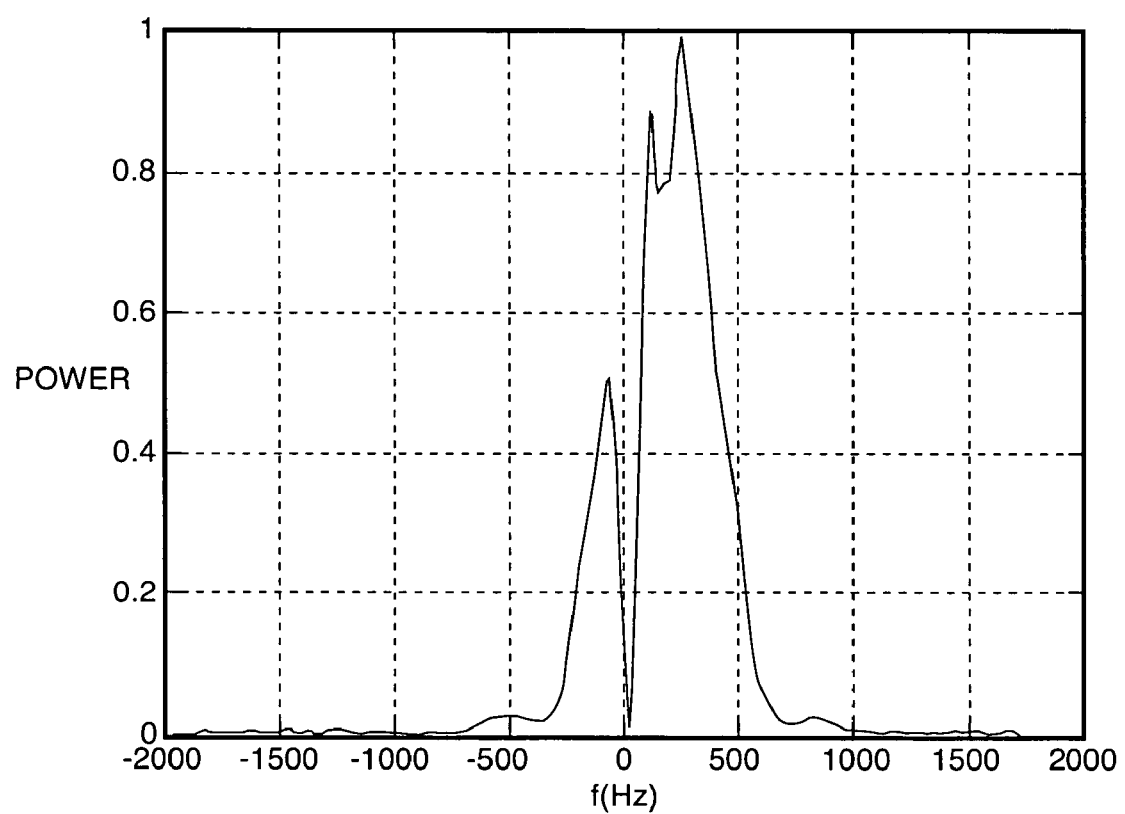
FIG. 5 illustrates ensemble averaged Doppler spectra obtained at a beam-vessel angle of 88°.

FIGS. 4 and 5 shows a comparison of typical ensemble (N=100) averaged Doppler spectra obtained from the reference beam at angles of approximately 90° and 88°, respectively. As shown, even a small deviation from 90° makes the Doppler spectrum strongly asymmetrical.

In the experiment of this example, the beam-to-flow angle was manually changed in steps of 1° around 90°. For each angle, the Symmetry index was estimated for: a) steady flow (volume flow: Q=250 ml/min); b) steady flow (Q=450 ml/min); c) pulsatile flow (Q=300 ml/min). During each acquisition, typically 2 seconds long, one SI was estimated every 20 ms. Table A reports the average SI measured for each angle in the range 85°-95°. This table clearly shows that the SI dramatically falls down for deviations of a few degrees from the transverse orientation.

TABLE A

| $\alpha$ [°] | | 85 | 86 | 87 | 88 | 89 | 90 | 91 | 92 | 93 | 94 | 95 |
|---|---|---|---|---|---|---|---|---|---|---|---|---|
| SI [%] | a) | 26 | 38 | 52 | 67 | 85 | 90 | 61 | 43 | 26 | 16 | 13 |
| | b) | 22 | 35 | 48 | 53 | 76 | 87 | 62 | 39 | 15 | 10 | 7 |
| | c) | 4 | 8 | 37 | 55 | 70 | 87 | 69 | 40 | 24 | 12 | 7 |

In order to evaluate the accuracy and precision attainable in Doppler angle estimation, once the flow conditions had been fixed, the probe was manually rotated until a "blind" operator estimated that the spectrogram was "symmetrical". Then, the actual deviation from the desired 90° beam-to-vessel angle (measurement error) was evaluated through a calibrated goniometer. This procedure was repeated for different steady and pulsatile flow conditions by 4 operators, two of them not being specifically trained for this. A set of 40 measurements was thus completed producing an rms error of 0.7°.

The accuracy of the experiment was confirmed by taking the SI into consideration while gradually changing the Doppler angle toward 90°. It was decided that the Doppler angle could be assumed to be 90° once the SI had overcome a threshold fixed at 85%. The corresponding error was estimated by measuring, through the calibrated goniometer, how far from 90° the probe was stopped. The mean error obtained from a group of 40 measurements was confirmed to be lower than 1°.

Velocity measurements were performed by using the steering angles available with the Megas system. In steady flow conditions (Q=300 ml/min), the reference beam was first set at an angle $\theta_2$ which was assumed to be 90° as soon as the SI appeared steadily >85%. Then the measuring beam was steered so that interbeam angles of −18°, +12°, +18° were established. Accordingly, the velocity from the SV in the tube center was estimated, by assuming $\theta_1$=72°, 78°, 108°. For each interbeam angle, the measurement was repeated 5 times by holding back the probe and readjusting the M-lines orientation between successive measures. Table B summarizes these results.

TABLE B

| | 72° $f_1 \cong 400$ Hz | 78° $f_1 \cong 500$ Hz | 108° $f_1 \cong 400$ Hz |
|---|---|---|---|
| velocity [cm/s] | 26.1 | 26.8 | 26.0 |
| | 26.2 | 26.8 | 25.9 |
| | 25.8 | 26.5 | 26.2 |
| | 26.0 | 26.6 | 26.5 |
| | 25.5 | 26.4 | 26.1 |

Figure 6:
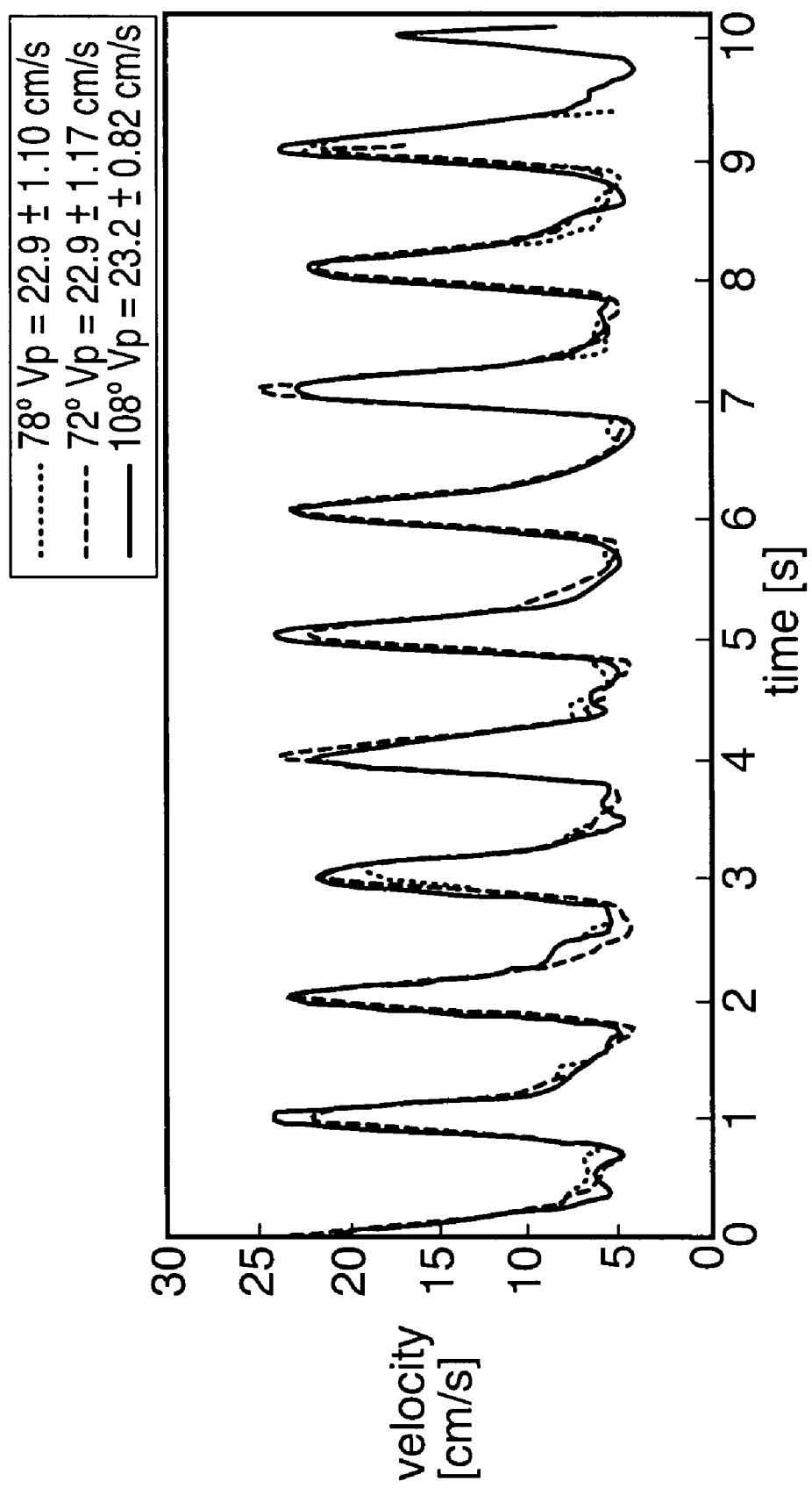
FIG. 6 illustrates velocity magnitudes recorded with a dual-beam system by employing 3 different interbeam angles.

A similar test was repeated for pulsatile flow conditions (Q@200 ml/min). The behavior of velocity magnitudes obtained at 3 different steering angles is shown in FIG. 6, which also reports the average velocity peaks and the SDs obtained from each acquisition.

I claim:

1. A method of measuring the rate of blood flow comprising the steps of:
    orienting a first ultrasound beam in a direction substantially perpendicular to the direction of the blood flow to be measured,
    evaluating the symmetry of the Doppler spectrum obtained from the backscattered echoes of said first ultrasound beam,
    reorienting responsive to said evaluated symmetry said first ultrasound beam such that the Doppler spectrum of the backscattered echoes of said first ultrasound beam is substantially symmetrical around the zero frequency,
    measuring the Doppler frequency of the backscattered echoes of a second ultrasound beam oriented at a fixed angle to said first reoriented ultrasound beam, and
    calculating the rate of blood flow based on said fixed angle and the measured Doppler frequency of the backscattered echoes of said second ultrasound beam.

2. The method of claim 1 wherein said first ultrasound beam is reoriented to be in a direction within about 2.degree. of perpendicular to the direction of the blood flow to be measured.

3. The method of claim 1 wherein said first ultrasound beam is reoriented to be in a direction within about 1.degree. of perpendicular to the direction of the blood flow to be measured.

4. The method of claim 3 wherein said first ultrasound beam is reoriented automatically.

5. The method of claim 3 wherein said first and second ultrasound beams are produced by a linear array probe.

6. The method of claim 5 further comprising the step of selecting a subaperture of said linear array probe for said second ultrasound beam to pass through.

7. The method of claim 1 further comprising the step of calculating the symmetry index of said first ultrasound beam.

8. The method of claim 7 further comprising the step of converting said symmetry index value to a signal for controlling an actuator.

9. A system for measuring the rate of blood flow comprising:
    a first ultrasonic transducer,
    a second ultrasonic transducer oriented at a fixed angle to said first ultrasonic transducer,
    a computer configured to determine when a Doppler frequency spectrum obtained from backscattered echoes of said first ultrasonic transducer is substantially symmetrical around a zero frequency, thereby indicating that a beam to flow angle of the first ultrasonic transducer is at approximately 90 degrees and calculate a beam to flow angle of said second ultrasonic transducer based on said indicated beam to flow angle of said first ultrasonic transducer and said fixed angle; and means for calculating the rate of blood flow based upon said beam to flow angle of said second ultrasonic transducer and Doppler frequency of backscattered echoes of said second ultrasonic transducer.

10. The system for measuring the rate of blood flow of claim 9 wherein said computer generates a viewable graphical representation of the symmetry of said Doppler spectrum around the zero frequency.

11. The system for measuring the rate of blood flow of claim 9 wherein said computer generates a viewable numerical representation of the symmetry of said Doppler spectrum around the zero frequency.

12. The system for measuring the rate of blood flow of claim 9 wherein said first ultrasonic transducer comprises a first subaperture of a linear array probe, and said second ultrasonic transducer comprises a second subaperture of said linear array probe.

13. The system for measuring the rate of blood flow of claim 11 further comprising an actuator for automatically reorienting said first ultrasonic transducer to an orientation substantially perpendicular to the rate of blood flow to be measured.

14. The system for measuring the rate of blood flow of claim 12 wherein said second subaperture is selectable from two or more subapertures.

* * * * *

UNITED STATES PATENT AND TRADEMARK OFFICE
CERTIFICATE OF CORRECTION

PATENT NO. : 7,591,787 B2  Page 1 of 1
APPLICATION NO. : 11/227662
DATED : September 22, 2009
INVENTOR(S) : Piero Tortoli It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 576 days.

Signed and Sealed this

Twenty-first Day of September, 2010

David J. Kappos
*Director of the United States Patent and Trademark Office*